(12) United States Patent
Ueno et al.

(10) Patent No.: US 8,871,752 B2
(45) Date of Patent: Oct. 28, 2014

(54) METHOD FOR MODULATING STEM CELL GROWTH

(75) Inventors: Ryuji Ueno, Montgomery, MD (US); Sachiko Kuno, Montgomery, MD (US)

(73) Assignee: Sucampo AG, Zug (CH)

( * ) Notice: Subject to any disclaimer, the term of this patent is extended or adjusted under 35 U.S.C. 154(b) by 123 days.

(21) Appl. No.: 12/388,048

(22) Filed: Feb. 18, 2009

(65) Prior Publication Data

US 2009/0209643 A1 Aug. 20, 2009

Related U.S. Application Data

(60) Provisional application No. 61/029,713, filed on Feb. 19, 2008.

(51) Int. Cl.
*A01N 43/00* (2006.01)
*A61K 31/33* (2006.01)
*A61K 31/5575* (2006.01)

(52) U.S. Cl.
CPC .................................. *A61K 31/5575* (2013.01)
USPC .......................................... 514/183; 514/557

(58) Field of Classification Search
None
See application file for complete search history.

(56) References Cited

U.S. PATENT DOCUMENTS

| | | | |
|---|---|---|---|
| 5,073,569 A | 12/1991 | Ueno et al. | |
| 5,166,174 A | 11/1992 | Ueno et al. | |
| 5,212,324 A | 5/1993 | Ueno | |
| 5,221,763 A | 6/1993 | Ueno et al. | |
| 5,703,108 A * | 12/1997 | Cameron et al. | 514/382 |
| 5,739,161 A | 4/1998 | Ueno | |
| 6,242,485 B1 | 6/2001 | Ueno | |
| 7,129,272 B2 | 10/2006 | Ueno et al. | |
| 2006/0247317 A1 | 11/2006 | Ueno | |

FOREIGN PATENT DOCUMENTS

| | | |
|---|---|---|
| TW | I284535 | 3/2000 |
| WO | 2006/080549 A2 | 8/2006 |
| WO | 2006093348 A2 | 9/2006 |
| WO | 2006101244 A2 | 9/2006 |
| WO | WO 2006093348 A2 * | 9/2006 |
| WO | 2007/070964 A1 | 6/2007 |
| WO | 2007/112084 A2 | 10/2007 |
| WO | 2008073748 A1 | 6/2008 |
| WO | 2008/108322 A2 | 9/2008 |
| WO | 2008/148938 A1 | 12/2008 |

OTHER PUBLICATIONS

Limke et al, Encyclopedia of life Science, 2005, John Wiley & Sons.*
Mattson et al , Ann N Y Acad Sci. 1999;893:154-75.*
European Office Action dated Sep. 25, 2013, issued in European Patent Application No. 09712320.2.
Gidali et al, The Effect of E Type Protaglandins on the Proliferation of Haemopoietic Stem Cells in Vivo, Cell and Tissue Kinetics, Jan. 1, 1977, pp. 365-373, vol. 10, No. 4.
Feheri et al, Prostagland in E2 as Stimulator of Haemopoietic Stem Cell Proliferation, Nature, Feb. 22, 1974, pp. 550-551, vol. 247, No. 442.
Examination Report from the Intellectual Property Office dated Sep. 16, 2013, issued in Taiwanese Patent Application No. 098105222.
Extended European Search Report dated Sep. 30, 2013, issued in European Patent Application No. 13178225.2.

* cited by examiner

*Primary Examiner* — Wu-Cheng Winston Shen
*Assistant Examiner* — Jean Cornet
(74) *Attorney, Agent, or Firm* — Sughrue Mion, PLLC (57) ABSTRACT

In one embodiment, provided is a composition including a prostaglandin compound for modulating stem cell proliferation and/or differentiation in a mammalian subject. In another embodiment, the instant application is directed to a composition which includes a prostaglandin compound for modulating proliferation and/or differentiation of stem cells of a mammalian subject, in which the stem cells are contacted directly or indirectly with the composition of the invention.

18 Claims, 1 Drawing Sheet

FIG. 1

Ointment Base

Compound A ointment

FIG 2

METHOD FOR MODULATING STEM CELL GROWTH

CROSS REFERENCES TO THE RELATED APPLICATIONS

This application claims priority from a provisional application filed Feb. 19, 2008 and assigned provisional Ser. No. 61/029,713. The whole contents of the provisional application are herein incorporated by reference.

TECHNICAL FIELD

The present invention relates to a method and composition for modulating stem cell growth.

BACKGROUND

Stem cells are undifferentiated, or immature cells that are capable of giving rise to multiple, specialized cell types and ultimately to terminally differentiated cells. Unlike any other cells, they are able to renew themselves such that essentially an endless supply of mature cell types can be generated when needed. Due to this capacity for self-renewal, stem cells are therapeutically useful for the regeneration and repair of tissues and organs. Stem cells have the potential for providing benefit in a variety of clinical settings.

Stem cells are classified according to their differentiation potential as pluripotent and multipotent. Embryonic stem cells (ESC) are well-known as a pluripotent stem cell, which can be differentiated into almost any type of cells in the organism. Multipotent stem cells such as bone marrow stem cells exist in the adult body. Although their growth and differentiation potential is limited, they are considered to play important roles in self-repair of damaged tissues. Translating these advantages of stem cells into clinical benefits faces many challenges, including efficient proliferation and differentiation into the desired cell type(s), maintaining genetic stability during long-term culture and ensuring the absence of potentially tumorigenic ESC from the final product. Modulation of growth and differentiation with low molecular weight compounds is one of the solutions for these problems.

Prostaglandins (hereinafter, referred to as PG(s)) are members of class of organic carboxylic acids, which are contained in tissues or organs of human or other mammals, and exhibit a wide range of physiological activity PGs found in nature (primary PGs) generally have a prostanoic acid skeleton as shown in the formula (A):

(A)

On the other hand, some of synthetic analogues of primary PGs have modified skeletons. The primary PGs are classified into PGAs, PGBs, PGCs, PGDs, PGRs, PGFs, PGGs, PGHs, PGIs and PGJs according to the structure of the five-membered ring moiety, and further classified into the following three types by the number and position of the unsaturated bond at the carbon chain moiety:
Subscript 1: 13,14-unsaturated-15-OH
Subscript 2: 5,6- and 13,14-diunsaturated-15-OH
Subscript 3: 5,6-, 13,14-, and 17,18-triunsaturated-15-OH.

Further, the PGFs are classified, according to the configuration of the hydroxyl group at the 9-position, into α type (the hydroxyl group is of an α-configuration) and β type (the hydroxyl group is of a β-configuration).

PGs are known to have various pharmacological and physiological activities, for example, vasodilatation, inducing of inflammation, platelet aggregation, stimulating uterine muscle, stimulating intestinal muscle, anti-ulcer effect and the like.

Some 15-keto (i.e., having oxo at the 15-position instead of hydroxy)-PGs and 13,14-dihydro (i.e., having single bond between the 13 and 14-position)-15-keto-PGs are known as the substances naturally produced by the action of enzymes during the metabolism of primary PGs.

However it is not known how the prostaglandin compound acts on the stem cells.

DISCLOSURE OF THE INVENTION

The present invention relates to a method for modulating stem cell proliferation and/or differentiation in a mammalian subject, which comprises administering to the subject in need thereof an effective amount of a prostaglandin compound.

The present invention also relates to a method for modulating proliferation and/or differentiation of stem cells of a mammalian subject, which comprises contacting said stem cells with an effective amount of a prostaglandin compound.

The present invention also relates to a composition for modulating stem cell proliferation and/or differentiation in a mammalian subject which comprises a prostaglandin compound.

The present invention also relates to a composition for modulating proliferation and/or differentiation of stem cells of a mammalian subject which comprises a prostaglandin compound, wherein the modulation is effected by contacting the composition with said stem cells.

The present invention relates to use of a prostaglandin compound for the manufacture of a pharmaceutical composition for modulating stem cell proliferation and/or differentiation in a mammalian subject.

The present invention relates to use of a prostaglandin compound for the manufacture of a pharmaceutical composition for modulating proliferation and/or differentiation of stem cells of a mammalian subject, wherein the modulation is effected by contacting the composition with said stem cells.

BRIEF DESCRIPTION OF THE DRAWINGS

The sections of the skin from the animals treated with ointment base (left panel) and Compound A ointment (right panel) were stained with anti-Ki67 antibody.

DETAILED DESCRIPTION OF THE INVENTION

The nomenclature of the prostaglandin compounds used herein is based on the numbering system of the prostanoic acid represented in the above formula (A).

The formula (A) shows a basic skeleton of the C-20 carbon atoms, but the present invention is not limited to those having the same number of carbon atoms. In the formula (A), the numbering of the carbon atoms which constitute the basic skeleton of the PG compounds starts at the carboxylic acid (numbered 1), and carbon atoms in the a-chain are numbered 2 to 7 towards the five-membered ring, those in the ring are 8 to 12, and those in the ω-chain are 13 to 20. When the number of carbon atoms is decreased in the a-chain, the number is deleted in the order starting from position 2; and when the number of carbon atoms is increased in the a-chain, compounds are named as substitution compounds having respective substituents at position 2 in place of the carboxy group (C-1). Similarly, when the number of carbon atoms is decreased in the ω-chain, the number is deleted in the order starting from position 20; and when the number of carbon atoms is increased in the ω-chain, the carbon atoms beyond position 20 are named as substituents. Stereochemistry of the compounds is the same as that of the above formula (A) unless otherwise specified.

In general, each of the terms PGD, PGE and PGF represents a PG compound having hydroxy groups at positions 9 and/or 11, but in the present specification, these terms also include those having substituents other than the hydroxy group at positions 9 and/or 11. Such compounds are referred to as 9-dehydroxy-9-substituted-PG compounds or 11-dehydroxy-11-substituted-PG compounds. A PG compound having hydrogen in place of the hydroxy group is simply named as 9- or 11-deoxy-PG compound.

As stated above, the nomenclature of the PG compounds is based on the prostanoic acid skeleton. However, in case the compound has a similar partial structure as a prostaglandin, the abbreviation of "PG" may be used. Thus, a PG compound of which a-chain is extended by two carbon atoms, that is, having 9 carbon atoms in the a-chain is named as 2-decarboxy-2-(2-carboxyethyl)-PG compound. Similarly, a PG compound having 11 carbon atoms in the a-chain is named as 2-decarboxy-2-(4-carboxybutyl)-PG compound. Further, a PG compound of which ω-chain is extended by two carbon atoms, that is, having 10 carbon atoms in the ω-chain is named as 20-ethyl-PG compound. These compounds, however, may also be named according to the IUPAC nomenclatures.

Examples of the analogs (including substituted derivatives) or derivatives include a PG compound of which carboxy group at the end of a-chain is esterified a compound of which a-chain is extended physiologically acceptable salt thereof a compound having a double bond at 2-3 position or a triple bond at position 5-6, a compound having substituent(s) at position 3, 5, 6, 16, 17, 18, 19 and/or 20; and a compound having lower alkyl or a hydroxy (lower) alkyl group at position 9 and/or 11 in place of the hydroxy group.

According to the present invention, preferred substituents at position 3, 17, 18 and/or 19 include alkyl having 1-4 carbon atoms, especially methyl and ethyl. Preferred substituents at position 16 include lower alkyl such as methyl and ethyl, hydroxy, halogen atoms such as chlorine and fluorine, and aryloxy such as trifluoromethylphenoxy. Preferred substituents at position 17 include lower alkyl such as methyl and ethyl, hydroxy, halogen atoms such as chlorine and fluorine, aryloxy such as trifluoromethylphenoxy. Preferred substituents at position 20 include saturated or unsaturated lower alkyl such as C1-4 alkyl, lower alkoxy such as C1-4 alkoxy, and lower alkoxy alkyl such as C1-4 alkoxy-C1-4 alkyl. Preferred substituents at position 5 include halogen atoms such as chlorine and fluorine. Preferred substituents at position 6 include an oxo group forming a carbonyl group. Stereochemistry of PGs having hydroxy, lower alkyl or hydroxy(lower)alkyl substituent at position 9 and/or 11 may be α, β or a mixture thereof.

Further, the above analogs or derivatives may be compounds having an alkoxy, cycloalkyl, cycloalkyloxy, phenoxy or phenyl group at the end of the ω-chain where the chain is shorter than the primary PGs.

A prostaglandin compound used in the present invention is represented by the formula (I):

(I)

wherein L, M and N are hydrogen, hydroxy, halogen, lower alkyl, hydroxy(lower)alkyl, lower alkanoyloxy or oxo, wherein at least one of L and M is a group other than hydrogen, and the five-membered ring may have at least one double bond;

A is —$CH_3$, or —$CH_2OH$, —$COCH_2OH$, —$COOH$ or a functional derivative thereof;

B is single bond, —$CH_2$—$CH_2$—, —CH=CH—, —C≡C—, —$CH_2$—$CH_2$—$CH_2$—, —CH=CH—$CH_2$—, —$CH_2$—CH=CH—, —C≡C—$CH_2$— or —$CH_2$—C≡C—;

Z is or single bond wherein $R_4$ and $R_5$ are hydrogen, hydroxy, halogen, lower alkyl, lower alkoxy or hydroxy(lower)alkyl, wherein $R_4$ and $R_5$ are not hydroxy and lower alkoxy at the same time;

$R_1$ is a saturated or unsaturated bivalent lower or medium aliphatic hydrocarbon residue, which is unsubstituted or substituted with halogen, alkyl, hydroxy, oxo, aryl or heterocyclic group, and at least one of carbon atom in the aliphatic hydrocarbon is optionally substituted by oxygen, nitrogen or sulfur; and Ra is a saturated or unsaturated lower or medium aliphatic hydrocarbon residue, which is unsubstituted or substituted with halogen, oxo, hydroxy, lower alkyl, lower alkoxy, lower alkanoyloxy, cyclo(lower)alkyl, cyclo(lower)alkyloxy, aryl, aryloxy, heterocyclic group or hetrocyclic-oxy group; lower alkoxy; lower alkanoyloxy; cyclo(lower)alkyl; cyclo(lower)alkyloxy; aryl; aryloxy; heterocyclic group; heterocyclic-oxy group.

A preferred compound used in the present invention is represented by the formula (II):

(II)

wherein L and M are hydrogen atom, hydroxy, halogen, lower alkyl, hydroxy(lower)alkyl, lower alkanoyloxy or oxo, wherein at least one of L and M is a group other than hydrogen, and the five-membered ring may have one or more double bonds;

A is —CH$_3$, or —CH$_2$OH, —COCH$_2$OH, —COOH or a functional derivative thereof;

B is single bond, —CH$_2$—CH$_2$—, —CH=CH—, —C≡C—, —CH$_2$—CH$_2$—CH$_2$—, —CH=CH—CH$_2$—, —CH$_2$—CH=CH—, —C≡C—CH$_2$— or —CH$_2$—C≡C—;

Z is or single bond wherein R$_4$ and R$_5$ are hydrogen, hydroxy, halogen, lower alkyl, lower alkoxy or hydroxy(lower)alkyl, wherein R$_4$ and R$_5$ are not hydroxy and lower alkoxy at the same time;

X$_1$ and X$_2$ are hydrogen, lower alkyl, or halogen;

R$_1$ is a saturated or unsaturated bivalent lower or medium aliphatic hydrocarbon residue, which is unsubstituted or substituted with halogen, alkyl, hydroxy, oxo, aryl or heterocyclic group, and at least one of carbon atom in the aliphatic hydrocarbon is optionally substituted by oxygen, nitrogen or sulfur;

R$_2$ is a single bond or lower alkylene; and

R$_3$ is lower alkyl, lower alkoxy, lower alkanoyloxy, cyclo(lower)alkyl, cyclo(lower)alkyloxy, aryl, aryloxy, heterocyclic group or heterocyclic-oxy group.

In the above formula, the term "unsaturated" in the definitions for R$_1$ and Ra is intended to include at least one or more double bonds and/or triple bonds that are isolatedly, separately or serially present between carbon atoms of the main and/or side chains. According to the usual nomenclature, an unsaturated bond between two serial positions is represented by denoting the lower number of the two positions, and an unsaturated bond between two distal positions is represented by denoting both of the positions.

The term "lower or medium aliphatic hydrocarbon" refers to a straight or branched chain hydrocarbon group having 1 to 14 carbon atoms (for a side chain, 1 to 3 carbon atoms are preferable) and preferably 1 to 10, especially 1 to 8 carbon atoms.

The term "halogen atom" covers fluorine, chlorine, bromine and iodine.

The term "lower" throughout the specification is intended to include a group having 1 to 6 carbon atoms unless otherwise specified.

The term "lower alkyl" refers to a straight or branched chain saturated hydrocarbon group containing 1 to 6 carbon atoms and includes, for example, methyl, ethyl, propyl, isopropyl, butyl, isobutyl, t-butyl, pentyl and hexyl.

The term "lower alkylene" refers to a straight or branched chain bivalent saturated hydrocarbon group containing 1 to 6 carbon atoms and includes, for example, methylene, ethylene, propylene, isopropylene, butylene, isobutylene, t-butylene, pentylene and hexylene.

The term "lower alkoxy" refers to a group of lower alkyl-O—, wherein lower alkyl is as defined above.

The term "hydroxy(lower)alkyl" refers to a lower alkyl as defined above which is substituted with at least one hydroxy group such as hydroxymethyl, 1-hydroxyethyl, 2-hydroxyethyl and 1-methyl-1-hydroxyethyl.

The term "lower alkanoyloxy" refers to a group represented by the formula RCO—O—, wherein RCO— is an acyl group formed by oxidation of a lower alkyl group as defined above, such as acetyl.

The term "cyclo(lower)alkyl" refers to a cyclic group formed by cyclization of a lower alkyl group as defined above but contains three or more carbon atoms, and includes, for example, cyclopropyl, cyclobutyl, cyclopentyl and cyclohexyl.

The term "cyclo(lower)alkyloxy" refers to the group of cyclo(lower)alkyl-O—, wherein cyclo(lower)alkyl is as defined above.

The term "aryl" may include unsubstituted or substituted aromatic hydrocarbon rings (preferably monocyclic groups), for example, phenyl, tolyl, xylyl. Examples of the substituents are halogen atom and halo(lower)alkyl, wherein halogen atom and lower alkyl are as defined above.

The term "aryloxy" refers to a group represented by the formula ArO—, wherein Ar is aryl as defined above.

The term "heterocyclic group" may include mono- to tricyclic, preferably monocyclic heterocyclic group which is 5 to 14, preferably 5 to 10 membered ring having optionally substituted carbon atom and 1 to 4, preferably 1 to 3 of 1 or 2 type of hetero atoms selected from nitrogen atom, oxygen atom and sulfur atom. Examples of the heterocyclic group include furyl, thienyl, pyrrolyl, oxazolyl, isoxazolyl, thiazolyl, isothiazolyl, imidazolyl, pyrazolyl, furazanyl, pyranyl, pyridyl, pyridazinyl, pyrimidyl, pyrazinyl, 2-pyrrolinyl, pyrrolidinyl, 2-imidazolinyl, imidazolidinyl, 2-pyrazolinyl, pyrazolidinyl, piperidino, piperazinyl, morpholino, indolyl, benzothienyl, quinolyl, isoquinolyl, purinyl, quinazolinyl, carbazolyl, acridinyl, phenanthridinyl, benzimidazolyl, benzimidazolinyl, benzothiazolyl, phenothiazinyl. Examples of the substituent in this case include halogen, and halogen substituted lower alkyl group, wherein halogen atom and lower alkyl group are as described above.

The term "heterocyclic-oxy group" means a group represented by the formula HcO—, wherein Hc is a heterocyclic group as described above.

The term "functional derivative" of A includes salts (preferably pharmaceutically acceptable salts), ethers, esters and amides.

Suitable "pharmaceutically acceptable salts" include conventionally used non-toxic salts, for example a salt with an inorganic base such as an alkali metal salt (such as sodium salt and potassium salt), an alkaline earth metal salt (such as calcium salt and magnesium salt), an ammonium salt; or a salt with an organic base, for example, an amine salt (such as methylamine salt, dimethylamine salt, cyclohexylamine salt, benzylamine salt, piperidine salt, ethylenediamine salt, ethanolamine salt, diethanolamine salt, triethanolamine salt, tris(hydroxymethylamino)ethane salt, monomethyl-monoethanolamine salt, procaine salt and caffeine salt), a basic amino acid salt (such as arginine salt and lysine salt), tetraalkyl ammonium salt and the like. These salts may be prepared by a conventional process, for example from the corresponding acid and base or by salt interchange.

Examples of the ethers include alkyl ethers, for example, lower alkyl ethers such as methyl ether, ethyl ether, propyl ether, isopropyl ether, butyl ether, isobutyl ether, t-butyl ether, pentyl ether and 1-cyclopropyl ethyl ether; and medium or higher alkyl ethers such as octyl ether, diethylhexyl ether, lauryl ether and cetyl ether; unsaturated ethers such as oleyl ether and linolenyl ether; lower alkenyl ethers such as vinyl ether, allyl ether; lower alkynyl ethers such as ethynyl ether and propynyl ether; hydroxy(lower)alkyl ethers such as hydroxyethyl ether and hydroxyisopropyl ether; lower alkoxy (lower)alkyl ethers such as methoxymethyl ether and 1-methoxyethyl ether; optionally substituted aryl ethers such as phenyl ether, tosyl ether, t-butylphenyl ether, salicyl ether, 3,4-di-methoxyphenyl ether and benzamidophenyl ether; and aryl(lower)alkyl ethers such as benzyl ether, trityl ether and benzhydryl ether.

Examples of the esters include aliphatic esters, for example, lower alkyl esters such as methyl ester, ethyl ester, propyl ester, isopropyl ester, butyl ester, isobutyl ester, t-butyl ester, pentyl ester and 1-cyclopropylethyl ester; lower alkenyl esters such as vinyl ester and allyl ester; lower alkynyl esters such as ethynyl ester and propynyl ester; hydroxy(lower)alkyl ester such as hydroxyethyl ester; lower alkoxy (lower) alkyl esters such as methoxymethyl ester and 1-methoxyethyl ester; and optionally substituted aryl esters such as, for example, phenyl ester, tolyl ester, t-butylphenyl ester, salicyl ester, 3,4-di-methoxyphenyl ester and benzamidophenyl ester; and aryl(lower)alkyl ester such as benzyl ester, trityl ester and benzhydryl ester.

The amide of A mean a group represented by the formula —CONR'R", wherein each of R' and R" is hydrogen, lower alkyl, aryl, alkyl- or aryl-sulfonyl, lower alkenyl and lower alkynyl, and include for example lower alkyl amides such as methylamide, ethylamide, dimethylamide and diethylamide; arylamides such as anilide and toluidide; and alkyl or aryl-sulfonylamides such as methylsulfonylamide, ethylsulfonylamide and tolylsulfonylamide.

Preferred examples of L and M include hydrogen, hydroxy and oxo, and especially, M is hydroxy and L is oxo which has a 5-membered ring structure of, so called, PGE type.

Preferred example of A is —COOH, its pharmaceutically acceptable salt, ester or amide thereof.

Preferred example of $X_1$ and $X_2$ are both being halogen atoms, and more preferably, fluorine atoms, so called 16,16-difluoro type.

Preferred $R_1$ is a hydrocarbon residue containing 1-10 carbon atoms, preferably 6-10 carbon atoms. Further, at least one carbon atom in the aliphatic hydrocarbon is optionally substituted by oxygen, nitrogen or sulfur. Examples of $R_1$ include, for example, the following groups:
—$CH_2$—$CH_2$—$CH_2$—$CH_2$—$CH_2$—$CH_2$—,
—$CH_2$—CH=CH—$CH_2$—$CH_2$—$CH_2$
—$CH_2$—$CH_2$—$CH_2$—$CH_2$—CH=CH—,
—$CH_2$—C≡C—$CH_2$—$CH_2$—$CH_2$—,
—$CH_2$—$CH_2$—$CH_2$—$CH_2$—O—$CH_2$—,
—$CH_2$—CH=CH—$CH_2$—O—$CH_2$—,
—$CH_2$—C≡C—$CH_2$—O—$CH_2$—,
—$CH_2$—$CH_2$—$CH_2$—$CH_2$—$CH_2$—$CH_2$—$CH_2$—,
—$CH_2$—CH=CH—$CH_2$—$CH_2$—$CH_2$—$CH_2$—,
—$CH_2$—$CH_2$—$CH_2$—$CH_2$—$CH_2$—CH=CH—,
—$CH_2$—C≡C—$CH_2$—$CH_2$—$CH_2$—$CH_2$—,
—$CH_2$—$CH_2$—$CH_2$—$CH_2$—CH($CH_3$)—$CH_2$—,
—$CH_2$—$CH_2$—$CH_2$—$CH_2$—CH($CH_3$)—$CH_2$—,
—$CH_2$—$CH_2$—$CH_2$—$CH_2$—$CH_2$—$CH_2$—$CH_2$—$CH_2$—,
—$CH_2$—CH=CH—$CH_2$—$CH_2$—$CH_2$—$CH_2$—$CH_2$
—$CH_2$—$CH_2$—$CH_2$—$CH_2$—$CH_2$—$CH_2$—CH=CH—,
—$CH_2$—C≡C—$CH_2$—$CH_2$—$CH_2$—$CH_2$—$CH_2$—, and
—$CH_2$—$CH_2$—$CH_2$—$CH_2$—$CH_2$—$CH_2$—CH($CH_3$)—$CH_2$—.

Preferred Ra is a hydrocarbon containing 1-10 carbon atoms, more preferably, 1-8 carbon atoms. Ra may have one or two side chains having one carbon atom.

Preferable compounds include Ra is substituted by halogen and/or Z is C=O in the formula (I), or one of X1 and X2 is substituted by halogen and/or Z is C=O in the formula (II).

Most preferred embodiment is a prostaglandin compound is 11-deoxy-13,14-dihydro-15-keto-16,16-difluoro-prostaglandin $E_1$ compound.

The configuration of the ring and the α- and/or ω chains in the above formula (I) and (II) may be the same as or different from that of the primary PGs. However, the present invention also includes a mixture of a compound having a primary type configuration and a compound of a non-primary type configuration.

In the present invention, the PG compound which is dihydro between 13 and 14, and keto (=O) at 15 position may be in the keto-hemiacetal equilibrium by formation of a hemiacetal between hydroxy at position 11 and keto at position 15.

For example, it has been revealed that when both of $X_1$ and $X_2$ are halogen atoms, especially, fluorine atoms, the compound contains a tautomeric isomer, bicyclic compound.

It such tautomeric isomers as above are present, the proportion of both tautomeric isomers varies with the structure of the rest of the molecule or the kind of the substituent present. Sometimes one isomer may predominantly be present in comparison with the other. However, it is to be appreciated that the present invention includes both isomers.

Further, the 15-keto-PG compounds used in the invention include the bicyclic compound and analogs or derivatives thereof.

The bicyclic compound is represented by the formula (III)

(III)

wherein, A is —$CH_3$, or —$CH_2OH$, —$COCH_2OH$, —COOH or a functional derivative thereof;
$X_1'$ and $X_2'$ are hydrogen, lower alkyl, or halogen;
Y is wherein $R_4'$ and $R_5'$ are hydrogen, hydroxy, halogen, lower alkyl, lower alkoxy or hydroxy(lower)alkyl, wherein $R_4'$ and $R_5'$ are not hydroxy and lower alkoxy at the same time.

$R_1$ is a saturated or unsaturated divalent lower or medium aliphatic hydrocarbon residue, which is unsubstituted or substituted with halogen, alkyl, hydroxy, oxo, aryl or heterocyclic group, and at least one of carbon atom in the aliphatic hydrocarbon is optionally substituted by oxygen, nitrogen or sulfur; and $R_2'$ is a saturated or unsaturated lower or medium aliphatic hydrocarbon residue, which is unsubstituted or substituted with halogen, oxo, hydroxy, lower alkyl, lower alkoxy, lower alkanoyloxy, cyclo(lower)alkyl, cyclo(lower)alkyloxy, aryl, aryloxy, heterocyclic group or hetrocyclic-oxy group; lower alkoxy; lower alkanoyloxy; cyclo(lower)alkyl; cyclo(lower)alkyloxy; aryl; aryloxy; heterocyclic group; heterocyclic-oxy group.

$R_3'$ is hydrogen, lower alkyl, cyclo(lower)alkyl, aryl or heterocyclic group.

Furthermore, while the compounds used in the invention may be represented by a formula or name based on keto-type regardless of the presence or absence of the isomers, it is to be noted that such structure or name does not intend to exclude the hemiacetal type compound.

In the present invention, any of isomers such as the individual tautomeric isomers, the mixture thereof, or optical isomers, the mixture thereof, a racemic mixture, and other steric isomers may be used in the same purpose.

Some of the compounds used in the present invention may be prepared by the method disclosed in U.S. Pat. Nos. 5,073,569, 5,166,174, 5,221,763, 5,212,324, 5,739,161 and 6,242,485 (these cited references are herein incorporated by reference).

An embodiment of the present invention includes a method for modulating stem cell proliferation and/or differentiation in a mammalian subject, which comprises administering to the subject in need thereof an effective amount of a prostaglandin compound.

The mammalian subject may be any mammalian subject including a human. The subject in need of the modulation of stem cell proliferation and/or differentiation may include, but not limited to, those suffered from a disease or condition in which the tissue or organ is damaged or defective. For example, the mammalian subject may be those suffered from osteoporosis, bone fracture, alveolar bone regeneration, anaplastic anemia and muscular dystrophy. Accordingly, the present invention also provides a method for the treatment of a disease or condition in which the tissue or organ is damaged or defective, for example, for the treatment of osteoporosis, bone fracture, alveolar bone regeneration, anaplastic anemia and muscular dystrophy.

The compound may be applied systemically or topically. Usually, the compound may be administered by oral administration, intranasal administration, inhalational administration, intravenous injection (including infusion), subcutaneous injection, intra rectal administration, intra vaginal administration, transdermal administration and the like.

The dose may vary depending on the strain of the animal, age, body weight, symptom to be treated, desired therapeutic effect, administration route, term of treatment and the like. A satisfactory effect can be obtained by systemic administration 1-4 times per day or continuous administration at the amount of 0.00001-500 mg/kg per day, more preferably 0.0001-100 mg/kg.

The compound may preferably be formulated in a pharmaceutical composition suitable for administration in a conventional manner. The composition may be those suitable for oral administration, intranasal administration, inhalational administration, injection or perfusion as well as it may be an external agent, suppository or pessary.

The composition of the present invention may further contain physiologically acceptable additives. Said additives may include the ingredients used with the present compounds such as excipient, diluent, filler, resolvent, lubricant, adjuvant, binder, disintegrator, coating agent, cupsulating agent, ointment base, suppository base, aerozoling agent, emulsifier, dispersing agent, suspending agent, thickener, tonicity agent, buffering agent, soothing agent, preservative, antioxidant, corrigent, flavor, colorant, a functional material such as cyclodextrin and biodegradable polymer, stabilizer. The additives are well known to the art and may be selected from those described in general reference books of pharmaceutics.

The amount of the above-defined compound in the composition of the invention may vary depending on the formulation of the composition, and may generally be 0.000001-10.0%, more preferably 0.00001-5.0%, most preferably 0.0001-1%.

Examples of solid compositions for oral administration include tablets, troches, sublingual tablets, capsules, pills, powders, granules and the like. The solid composition may be prepared by mixing one or more active ingredients with at least one inactive diluent. The composition may further contain additives other than the inactive diluents, for example, a lubricant, a disintegrator and a stabilizer. Tablets and pills may be coated with an enteric or gastroenteric film, if necessary. They may be covered with two or more layers. They may also be adsorbed to a sustained release material, or microcapsulated. Additionally, the compositions may be capsulated by means of an easily degradable material such gelatin. They may be further dissolved in an appropriate solvent such as fatty acid or its mono, di or triglyceride to be a soft capsule. Sublingual tablet may be used in need of fast-acting property.

Examples of liquid compositions for oral administration include emulsions, solutions, suspensions, syrups and elixirs and the like. Said composition may further contain a conventionally used inactive diluents e.g. purified water or ethyl alcohol. The composition may contain additives other than the inactive diluents such as adjuvant e.g. wetting agents and suspending agents, sweeteners, flavors, fragrance and preservatives.

The composition of the present invention may be in the form of spraying composition, which contains one or more active ingredients and may be prepared according to a known method.

Example of the intranasal preparations may be aqueous or oily solutions, suspensions or emulsions comprising one or more active ingredient. For the administration of an active ingredient by inhalation, the composition of the present invention may be in the form of suspension, solution or emulsion which can provide aerosol or in the form of powder suitable for dry powder inhalation. The composition for inhalational administration may further comprise a conventionally used propellant.

Examples of the injectable compositions of the present invention for parenteral administration include sterile aqueous or non-aqueous solutions, suspensions and emulsions. Diluents for the aqueous solution or suspension may include, for example, distilled water for injection, physiological saline and Ringer's solution.

Non-aqueous diluents for solution and suspension may include, for example, propylene glycol, polyethylene glycol, vegetable oils such as olive oil, alcohols such as ethanol and polysorbate. The composition may further comprise additives such as preservatives, wetting agents, emulsifying agents, dispersing agents and the like. They may be sterilized by filtration through, e.g. a bacteria-retaining filter, compounding with a sterilizer, or by means of gas or radioisotope irradiation sterilization. The injectable composition may also be provided as a sterilized powder composition to be dissolved in a sterilized solvent for injection before use.

The present external agent includes all the external preparations used in the fields of dermatology and otolaryngology, which includes ointment, cream, lotion and spray.

Another form of the present invention is suppository or pessary, which may be prepared by mixing active ingredients into a conventional base such as cacao butter that softens at body temperature, and nonionic surfactants having suitable softening temperatures may be used to improve absorbability.

Another embodiment of the present invention includes a method for modulating proliferation and/or differentiation of stem cells of a mammalian subject, which comprises contacting said stem cells with an effective amount of a prostaglandin compound.

The method can be used on cells in culture, e.g. in vitro or ex vivo. For example, stem cells or progenitor cells can be cultured in vitro in culture medium and the contacting step can be effected by adding one or more prostaglandin compounds to the culture medium in a amount sufficient to modulate one or more of proliferation, survival and/or differentiation, e.g. at the amount of $1 \times 10^{-12} - 1 \times 10^{-3}$ mol/l. According to the present invention, the cells may be contacted concomitantly with the compound of the present invention and the one or more stem cell modulators, or the cells may be contacted sequentially.

The method of modulating stem cell proliferation and/or differentiation may further comprise administering to the subject with one or more stem cell modulators in order to modulate proliferation and/or differentiation the stem cells.

The method of the present invention can be used to stimulate the ex vivo expansion and/or differentiation of stem cells and thereby provide a population of cells suitable for transplantation or administration to a subject in need thereof. Ex vivo expansion of stem cells has therapeutic indications for treating numerous disease conditions.

The method of modulating proliferation and/or differentiation of stem cells may also be used in vivo to modulate proliferation and/or differentiation of resident stem cells in tissues and thereby aid in the replacement or repair of tissue damaged as a result of the disease or disorder, or after surgery or injury and so on.

Sequential methods that modulate proliferation and subsequent differentiation of stem cells are also contemplated. For example, a stem cell population may be expanded ex vivo by contacting the cells, directly or indirectly, with a prostaglandin compound.

The method of the present invention may be employed in the regeneration therapy. The expanded population of cells is subsequently administered to a subject and treated in vivo with one or more stem cell modulators that promotes differentiation of the stem cells in situ. Alternatively, both steps may be conducted ex vivo prior to administration of the cells to a subject.

For in vivo and ex vivo methods, the stem cells can be autologous, allogeneic or xenogeneic.

Therapeutic applications of the method typically pertain to situations where there is a need to replace lost or damaged tissue, for example, after chemotherapy or radiation therapy, after muscle or skin injury, or in the treatment or management of diseases and disorders. For example, the methods can be used in the treatment, management or prevention of neurodegenerative disorders, such as degenerative bone diseases such as osteoporosis; bone fracture, alveolar bone regeneration; anaplastic anemia and muscular dystrophy.

The term "stem cell modulator" as used herein, refers to a compound that is capable of stimulating or inhibiting stem cell proliferation, differentiation, or both proliferation and differentiation.

The term "stem cell" as used herein, includes human origin or stem cells of non-human mammalian origin and refers to a cell that is capable of differentiating into one or more differentiated cell types. The stem cells may be pluripotent stem cells having the capacity to develop into any cell type, or they may be multipotent stem cells having the capacity to differentiate into several different, final differentiated cell types and derived from a particular tissue or organ, for example, from blood, nerve, skeletal muscle, cardiac muscle, bone marrow, skin, gut, bone, kidney, liver, pancreas, thymus, and the like. Pluripotent stem cells are usually embryonic stem cells in origin and multiipotent stem cells include somatic stem cells such as mesenchymal stem cells, bone marrow stem cells, adipose derived stem cells, hemopoietic stem cells, epidermal stem cells and neuronal stem cells. According to the instant invention, stem cells may preferably be neuronal stem cells, epidermal stem cells and mesenchymal stem cells.

The term "progenitor cell" as used herein, refers to a cell that is committed to a particular cell lineage and which gives rise to a particular limited range of differentiated cell types by a series of cell divisions. An example of a progenitor cell would be amyoblast, which is capable of differentiation to only one type of cell, but is itself not fully mature or fully differentiated.

The terms "proliferation" as used interchangeably herein with reference to cells, refer to an increase in the number of cells of the same type by cell division.

The term "differentiation" as used herein, refers to a developmental process whereby cells become specialized for a particular function, for example, where cells acquire one or more morphological characteristics and/or functions different from that of the initial cell type.

The pharmaceutical composition of the present invention may further contain other pharmacological ingredients as far as they do not contradict the purpose of the present invention.

Further details of the present invention will follow with reference to test example, which, however, is not intended to limit the present invention.

TEST EXAMPLE 1

The effect of Compound A (11-deoxy-13,14-dihydro-15-keto-16,16-difluoro-PGE$_1$) on impaired neuron was tested. 1-methyl-4-phenyl-1,2,3,6-tetrahydropyridine hydrochloride (MPTP) was intraperitoneally administered to male C57BL/6 mice aged 10 weeks at 15 mg/kg/dose 4 times a day with an approximately 3-hour interval between doses for 2 days (experimental Day 1 and Day 2) to destroy the dopaminergic neuron in the brain. On the day following the final MPTP administration (on Day 3), some MPTP-treated mice were sacrificed to estimate the severity of degeneration and loss of nigro-striatal dopamine neurons by measuring the area of tyrosine hydroxylase (TH)-positive immunostained fibers in striatum. Other MPTP-treated mice were orally administered Compound A (11-deoxy-13,14-dihydro-15-keto-16,16-difluoro-PGE$_1$) or the vehicle twice a day for 5 days (from Day 3 to Day 7) starting from the day following the final MPTP administration. The mice were decapitated on the day following the final administration of Compound A or the vehicle (on Day 8), and the whole brain was removed by incision of the skull, and placed into Bouin's fluid (pH 3.5-4.0). The brain section at the level of striatum (0.74 mm anterior to bregma) and substantia nigra (3.08 mm posterior to bregma) was cut out. After dehydration, the paraffin embedding of the slices was employed. Sections (about 6 μm thick) were prepared out of each of the slices at Bregma 0.74 mm and Bregma −3.08 mm, and the sections were used for TH immunostaining. The number of TH-positive immunostained cells in the right substantia nigra compacta (SNC) at Bregma −3.08 mm was counted by visual observation using an optical microscope OLYMPUS BH-2 (Olympus Corp.) with a ×20 microscope objective. For measuring the area of TH-positive immunostained fibers in striatum, an image obtained with an optical microscope OLYMPUS BH-2 (Olympus Corp.) with a ×40 microscope objective of TH-positive immunostained fibers in the right caudate putamen (CPu) at Bregma 0.74 mm was incorporated into a computer through OLYMPUS MCD-350, and the area of TH-positive fibers larger than 5 μm² was measured using an image analyzer Win ROOF (V5.6, Mitani Corp.), and expressed in term of an area of 1 mm².

On the day following the final MPTP administration (on Day 3), the MPTP-treated mice already showed a significant decrease in the area of TH-positive immunostained fibers in the striatum (0.0168±0.0029 mm²) as compared to the normal mice (0.0758±0.0182 mm²), and thus the degeneration and loss of the nigro-striatal dopaminergic neurons were already observed on Day 3 by the MPTP treatment for 2 days.

As shown in Table 1, after the treatment period (on Day 8), a significantly smaller area of TH-positive fibers in the striatum was observed in the "MPTP+Vehicle (control)" group compared to the "Physiological saline+Vehicle (control)" group. The area of the "MPTP+Vehicle (control)" group was similar to that observed in the MPTP-treated mice on Day 3. On the other hand, the "MPTP+Compound A at 0.1 mg/kg" group and the "MPTP+Compound A at 1 mg/kg" group showed a significantly greater mean area of TH-positive fibers in the striatum compared to the "MPTP+Vehicle (control)" group.

As shown in Table 2, Compound A increased the number of TH-positive immunostained cells in the substantia nigra in a dose-dependent manner.

The results show that Compound A restores the impaired neuron. Further more, the results indicate that Compound A facilitates proliferation and differentiation of stem cells and regenerate the impaired tissues.

TABLE 1

Effects of oral administration of Compound A on area of TH-positive immunostained fibers of striatum in the MPTP-treated mice.

| Group | n | Area of TH-positive immunostained fibers in striatum (mm2), mean ± S.E. |
|---|---|---|
| Physiological saline + Vehicle (Control) | 10 | 0.1432 ± 0.0223 |
| MPTP + Vehicle (Control) | 10 | 0.0117 ± 0.0029** |
| MPTP + Compound A at 0.1 mg/kg | 10 | 0.0465 ± 0.0102## |
| MPTP + Compound A at 1 mg/kg | 10 | 0.0444 ± 0.0092## |

TABLE 2

Effects of oral administration of Compound A on number of TH-positive immunostained cells of substantia nigra in the MPTP-treated mice.

| Group | n | TH-positive immunostained cells in substantia nigra (Number of cells), mean ± S.E. |
|---|---|---|
| Physiological saline + Vehicle (Control) | 10 | 54.1 ± 2.7 |
| MPTP + Vehicle (Control) | 10 | 34.2 ± 5.0** |
| MPTP + Compound A at 0.1 mg/kg | 10 | 35.2 ± 5.0 |
| MPTP + Compound A at 1 mg/kg | 10 | 44.4 ± 5.0 |

TEST EXAMPLE 2

The effect of Compound A (11-deoxy-13,14-dihydro-15-keto-16,16-difluoro-PGE$_1$) on excisional wound healing was tested. A full-thickness excisional wound (1.5×1.5 cm) was made on the back of female diabetic (BKS.Cg-+Lepr$^{db}$/+Lepr$^{db}$/Jcl) mice at the age of 12 weeks. The excisional wound was covered with the perforated film dressing. Each test ointment was put into a 1-mL disposable polypropylene syringe to which a 21 G hypodermic needle is attached, and 0.1 mL of the test ointment was applied to the wound by sticking the hypodermic needle into the film dressing, which covers the excisional wound. The application was performed once a day for 21 days starting from the day when the excisional wound was made; the day when the excisional wound was made was defined as Day 1. For histological examination, the skin including the excisional wound was obtained from animals treated with each test ointment for 6 days, and was served for immunostaining with antibody against Ki67, a marker protein of proliferating cells. The outline of each excisional wound was traced before application (Day 1) and Days 6, 8, 11, 13, 15, 18, 20, and 22 of administration. The traced excisional wound area was measured with an area-line meter. The wound area on each day of measurement was expressed as a ratio of the wound area on Day 1 as 100%, and the area under the wound area (%)-time curve (AUC) was calculated by using a trapezoid method.

Figure 1:
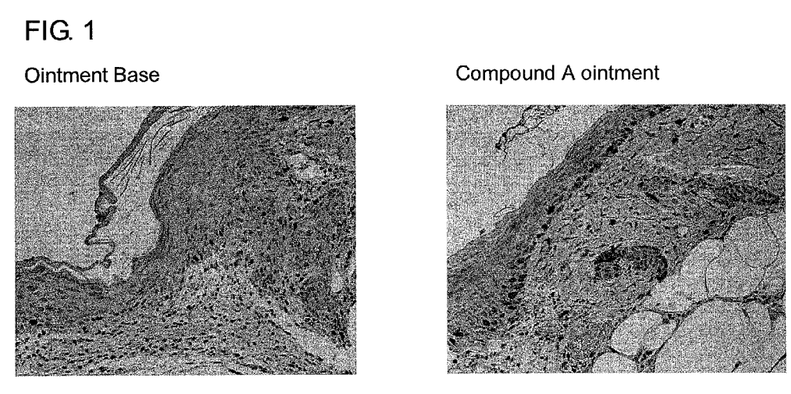
FIG. 1 represents result of Test Example 2, effect of Compound A (11-deoxy-13,14-dihydro-15-keto-16,16-difluoro-$PGE_1$) ointment on excisional wound healing in diabetic mice.

Marked increase of proliferating (Ki67-positive) cells in the epidermis was observed in the Compound A ointment group than the ointment base group (FIG. 1). Since the epidermis is believed to contain only two types of proliferating cells: stem cells and their transit amplifying progeny (transit amplifying cells), this result indicates that Compound A stimulated proliferation of stem cells or differentiation to their progeny.

With such stimulatory activity, Compound A accelerated skin wound healing (Table 3).

TABLE 3

Effect of compound A ointment on excisional wound healing in diabetic mice.

| Group | Concentration micro-g/g | n | AUC$_{Day1-22}$ Mean ± S.E. |
|---|---|---|---|
| Ointment base | — | 10 | 1168.8 ± 42.4 |
| Compound A ointment | 10 | 10 | 965.4 ± 26.4** |
| Compound A ointment | 100 | 10 | 988.0 ± 22.0* |

*p < 0.05,
**p < 0.01 compared with ointment base

TEST EXAMPLE 3

Effect of Compound A (11-deoxy-13,14-dihydro-15-keto-16,16-difluoro-PGE$_1$) on the osteoblast differentiation of mesenchymal stem cells was tested.

Method

Human bone marrow donor samples was obtained to initiate the production of mesenchymal stem cell (MSC) for the study. The MSCs was then expanded in tissue culture flasks. The Compound A in DMSO and kept frozen at −20° C. until used, were diluted into medium so that final concentrations were 5 nM, 10 nM, and 50 nM in each well. To determine the effect of compound A on osteoblast differentiation, MSCs (1×10⁶/ml) were first cultured in medium in 24-well plates for 48 h. After allowing the cells to adhere to the growth surface, the medium was gently removed and 100 μl of each compound A dilution was added to 4 replicate wells. Osteoblast Culture Medium was then added (0.9 ml) and the cells incubated.

For this study, osteoblast detection was performed using 2 different markers. These were alkaline phosphase (AP) and osteocalcin (OC). Osteoblast detection required flow cytometry. Both markers were conjugated to phycoerythrin (PE) which emits fluorescence light in the 530 nm range.

After 14 days in culture, the medium of cultures was discarded. The cells were harvested by incubation for 15 min at 37° C. with 10 mM EDTA, and cells Those cells used for detection of AP+ osteoblasts were incubated for 45 min with 101 of anti-human alkaline phosphatase-PE antibody at 4° C. After incubation, the cells were washed once with 4 ml of PBS and resuspended in approx. 400 μl of PBS for flow cytometric analysis.

The second set of cells were used to detect osteocalcin. The cells were first fixed in 4% paraformaldehyde for 10 min. and further incubated in PBS containing 0.1% saponin to permeabilize and maintain permeabilization while the cells were incubated in the presence of anti-human osteocalcin-PE monoclonal antibody for 45 min in the dark. The cells were washed with 2 ml of saponin-containing PBS and resuspended in approx. 0.5 ml PBS for flow cytometric analysis.

RESULTS

Figure 2:
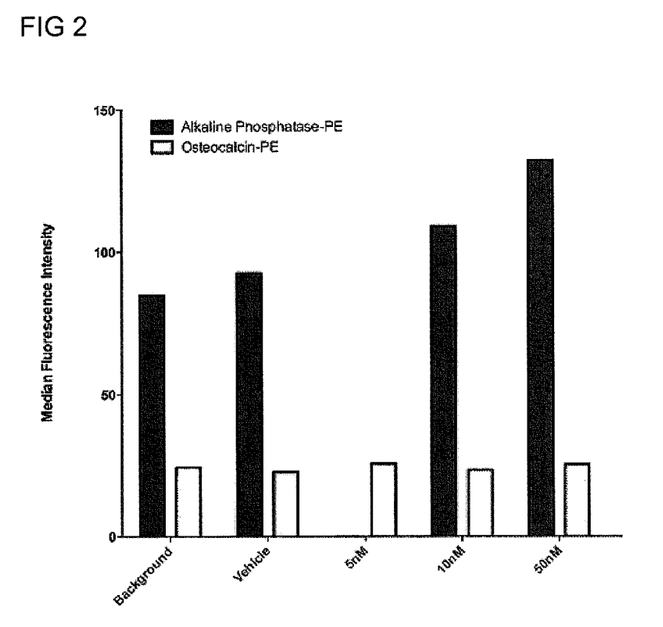
FIG. 2 represents result of Test Example 3, effect of (11-deoxy-13,14-dihydro-15-keto-16,16-difluoro-$PGE_1$) on the osteoblast differentiation of mesenchymal stem cells.

FIG. 2 shows the effect of Compound A on osteoblast differentiation as detected using both AP-PE and OC-PE. FIG. 2 shows the median fluorescence intensity. The AP-PE marker indicated that with increasing Compound A doses, there is an increase in AP up to 50 mM. This increase is above that obtained for the background or vehicle control. Therefore, Compound A results in a potentiation in fluorescence intensity of alkaline phosphatase, which indicates stimulation of osteoblast differentiation from MSCs.

What is claimed is:

1. A method for treating a disease or condition selected from the group consisting of osteoporosis, bone fracture, alveolar bone regeneration and anaplastic anemia in a mammalian subject, which comprises administering to the subject in need thereof an effective amount of a prostaglandin compound represented by the formula (I):

(I)

wherein L, M and N are hydrogen atom, hydroxy, halogen atom, lower alkyl, hydroxy(lower)alkyl, lower alkanoyloxy or oxo, wherein at least one of L and M is a group other than hydrogen, and the five-membered ring may have at least one double bond;

A is —$CH_3$, or —$CH_2OH$, —$COCH_2OH$, —COOH or a salt, ether, ester or amide thereof;

B is single bond, —$CH_2$—$CH_2$—, —CH=CH—, —C≡C—, —$CH_2$—$CH_2$—$CH_2$—, —CH=CH—$CH_2$—, —$CH_2$—CH=CH—, —C≡C—$CH_2$— or —$CH_2$—C≡C—;

Z is or single bond wherein $R_4$ and $R_5$ are hydrogen, hydroxy, halogen, lower alkyl, lower alkoxy or hydroxy(lower)alkyl, wherein $R_4$ and $R_5$ are not hydroxy and lower alkoxy at the same time;

$R_1$ is a saturated or unsaturated bivalent lower or medium aliphatic hydrocarbon residue, which is unsubstituted or substituted with halogen, alkyl, hydroxy, oxo, aryl or heterocyclic group, and at least one of carbon atom in the aliphatic hydrocarbon is optionally substituted by oxygen, nitrogen or sulfur; and Ra is a saturated or unsaturated lower or medium aliphatic hydrocarbon residue, which is unsubstituted or substituted with halogen, oxo, hydroxy, lower alkyl, lower alkoxy, lower alkanoyloxy, cyclo(lower)alkyl, cyclo(lower)alkyloxy, aryl, aryloxy, heterocyclic group or hetrocyclic-oxy group; lower alkoxy; lower alkanoyloxy; cyclo(lower)alkyl; cyclo(lower)alkyloxy; aryl; aryloxy; heterocyclic group; heterocyclic-oxy.

2. The method as described in claim 1, wherein said prostaglandin compound is a 16-mono or dihalogen-prostaglandin compound.

3. The method as described in claim 1, wherein said prostaglandin compound is a 15-keto-prostaglandin compound.

4. The method as described in claim 1, wherein said prostaglandin compound is a 13,14-dihydro-16-mono or dihalogen-prostaglandin compound.

5. The method as described in claim 1, wherein said prostaglandin compound is a 13,14-dihydro-15-keto-prostaglandin compound.

6. The method as described in claim 1, wherein said prostaglandin compound is a 13,14-dihydro-15-keto-16-mono or dihalogen-prostaglandin compound.

7. The method as described in claim 1, wherein said prostaglandin compound is a 13,14-dihydro-16-mono or difluoro-prostaglandin compound.

8. The method as described in claim 1, wherein said prostaglandin compound is a 15-keto-16-mono or difluoro-prostaglandin compound.

9. The method as described in claim 1, wherein said prostaglandin compound is a 13,14-dihydro-15-keto-16-mono or difluoro-prostaglandin compound.

10. The method as described in claim 1, wherein said prostaglandin compound is a 13,14-dihydro-16-mono or dihalogen-prostaglandin E compound.

11. The method as described in claim 1, wherein said prostaglandin compound is a 15-keto-16-mono or dihalogen-prostaglandin E compound.

12. The method as described in claim 1, wherein said prostaglandin compound is a 13,14-dihydro-15-keto-16-mono or dihalogen-prostaglandin E compound.

13. The method as described in claim 1, wherein said prostaglandin compound is a 13,14-dihydro-16,16-difluoro-prostaglandin $E_1$ compound.

14. The method as described in claim 1, wherein said prostaglandin compound is a 13,14-dihydro-15-keto-prostaglandin $E_1$ compound.

15. The method as described in claim 1, wherein said prostaglandin compound is a 11-deoxy-13,14-dihydro-15-keto-16,16-difluoro-prostaglandin $E_1$ compound.

16. The method as described in claim 1, wherein said prostaglandin compound is 11-deoxy-13,14-dihydro-15-keto-16,16-difluoro prostaglandin $E_1$, or a salt, ester or amide thereof.

17. The method as described in claim 1, wherein said prostaglandin compound is 11-deoxy-13,14-dihydro-15-keto-16,16-difluoro prostaglandin $E_1$.

18. The method as describe in claim 1, wherein said method stimulates osteoblast differentiation of mesenchymal stem cells.

* * * * *